United States Patent [19]

Thorup

[11] 4,048,723
[45] Sept. 20, 1977

[54] DENTAL EXPLORER

[76] Inventor: Palle Thorup, 20, Odensevej, 5750 Ringe, Denmark

[21] Appl. No.: 613,293

[22] Filed: Sept. 15, 1975

[30] Foreign Application Priority Data

Sept. 14, 1974 United Kingdom .............. 40139/74
Aug. 20, 1975 Denmark ........................... 3744/75

[51] Int. Cl.$^2$ ............................................. A61C 3/00
[52] U.S. Cl. ................................................. 32/40 R
[58] Field of Search .......................... 32/40 R, 50, 58; 128/276

[56] References Cited

U.S. PATENT DOCUMENTS

| | | | |
|---|---|---|---|
| 2,874,470 | 2/1959 | Richards | 32/58 |
| 3,032,879 | 5/1962 | Lafitte | 32/69 |
| 3,807,048 | 4/1974 | Malmin | 32/40 R |
| 3,919,775 | 11/1975 | Malmin | 32/40 R |
| 3,924,335 | 12/1975 | Balamuth | 32/58 |
| 3,935,640 | 2/1976 | Cohan | 32/40 R |

OTHER PUBLICATIONS

Arista Dental Catalogue, p. 7, Explorers, Arista Surgical Co., 67 Lexington Ave., N.Y., N.Y. 10010.

Primary Examiner—Robert Peshock
Attorney, Agent, or Firm—Browdy and Neimark

[57] ABSTRACT

A dental explorer comprising a handle with a generally tapered explorer portion which terminates in a point has been provided with a passage extending through the handle and through and/or alongside the explorer portion so that it terminates spaced from and generally directed against the point of the explorer portion. The other end of the passage is connected to a source of pressurized air through a light and flexible connection. In the passage or the connection is provided at least one valve which may be operated by the dentist for selectively admitting air therethrough. The explorer portion comprising the point may be detachably secured to the handle so as to allow it to be replaced by another similar or different explorer portion.

12 Claims, 4 Drawing Figures

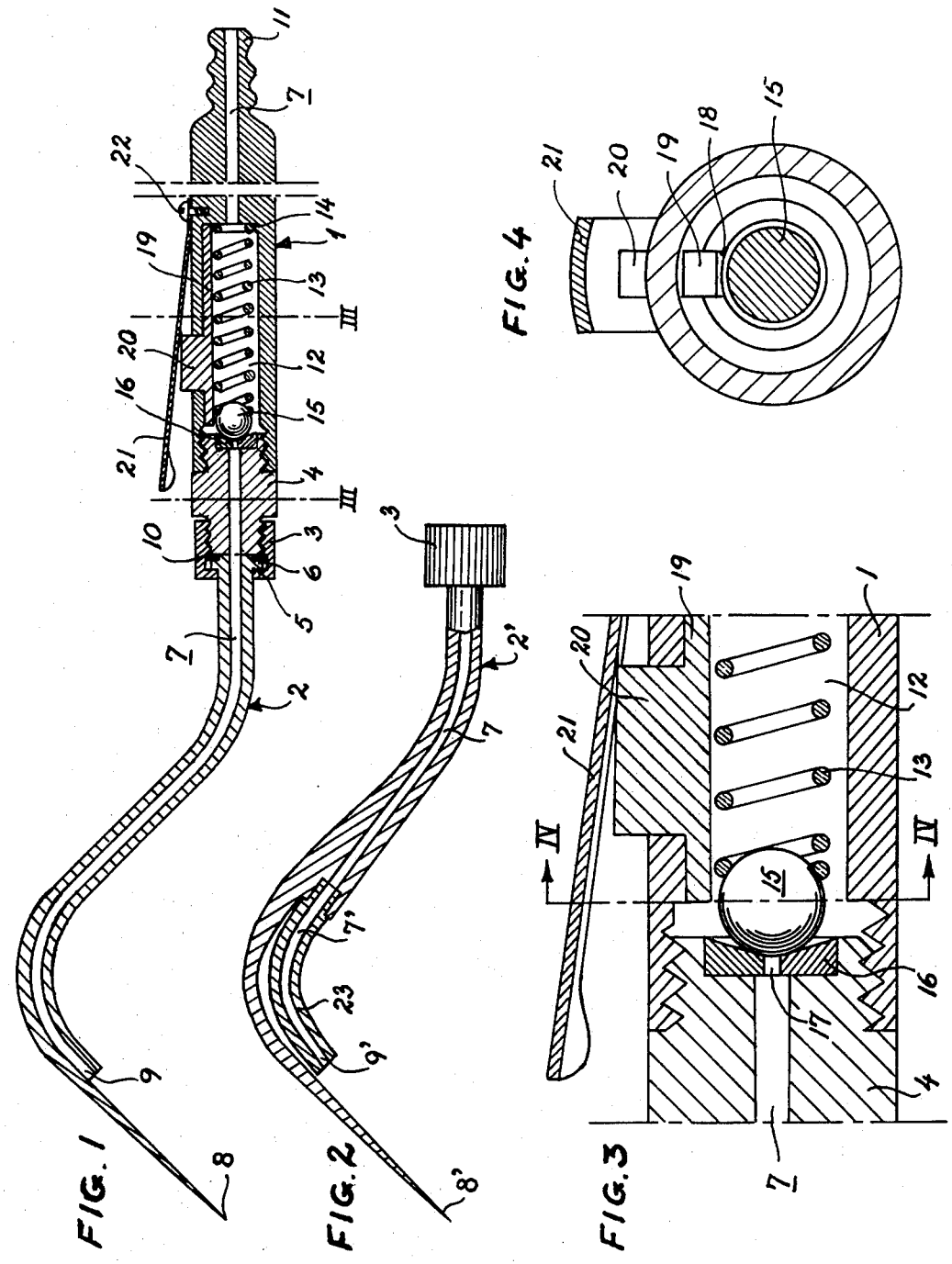

DENTAL EXPLORER

The present invention relates to a dental explorer for use in examining and/or treating teeth, comprising a handle or butt having a generally tapered explorer portion terminating in a point.

Explorers of this type are used for such purposes as diagnosing caries of the teeth, ascertaining whether a surgical caries treatment (drilling a tooth) has been performed to a caries-free depth in the tooth substance and checking teeth below the gum margin for the presence of tartar.

In view of the fact that it must be possible to use the explorer of tooth surfaces hard to get at, such as the posterior tooth surfaces, the tapered explorer portion is often provided with angular bends or "elbows" whereby the explorer point forms an angle to the longitudinal axis of the handle or butt.

The examination itself, the "exploration", is based inter alia on the resistance encountered by the explorer point when moved relatively to the tooth section examined. Hence, as an example, the resistance encountered by the explorer point when subject to a certain contact pressure it is moved across a tooth surface, or the resistance to penetration into the tooth substance when drilling a tooth. This resistance is judged by the dentist on the basis of both visual and tactile impressions, and, among other things, for this reason it may in a given case be important that the explorer poing is resilient in relation to the handle or butt. It is likewise important that the tooth section, e.g. a tooth surface, being examined should as far as possible be kept dry during the examination. In practice this is achieved by the dentist directing an air jet towards the area examined by means of a so-called "chip blower", e.g. of the type disclosed by German Pat. No. 1,061,959. Such a chip blower is actually a specially designed air gun connected by a tube to a compressed-air source and which comprises a handle, a finger-operated pneumatic valve and a nozzle which may be adjustable to allow the air jet to be directed towards tooth sections hard to get at.

Although drying of the tooth area examined by means of an air jet must generally be deemed both expedient and effective, this drying process, when performed as described above, involves a number of drawbacks associated with the fact that the examining dentist is required simultaneously or consecutively to use two instruments, viz. the explorer and the chip blower. Hence, the dentist is either forced to work with one instrument in each hand, dividing his attention between use of these two instruments, or must, if it is otherwise necessitated during the examination that he keep one hand free — such as for using a mirror or detaining mouth —, use the other hand for alternately gripping now one instrument and now the other. In the first place, this means that the dentist cannot give his full attention to the actual examination by means of the explorer, which might result in less certain diagnostics of e.g. caries in tooth surfaces hard to get at, and secondly, in connection with the aforesaid, the time consumed by the examination and other dental treatment is rendered substantially longer than desirable, i.e. essentially longer than the time consumed by the actual examination and treatment.

It has surprisingly been found that by means of a dental explorer of the type described by way of introduction it is possible in a simple manner to overcome these problems so that for his examination the dentist is merely required to use but one instrument and therefore at all times has one hand free and can give his full attention to the examination itelf by means of the explorer, the time consumed by the examination or treatment respectively being thereby substantially reduced in relation to the time consumed heretobefore. This is achieved in the dental explorer according to the invention by means of a passage extending through the handle or butt and through and/or lengthwise of the explorer portion and which terminates spaced from and generally oriented towards its point, said passage being at its opposite end connected to a compressed-air source through a light and flexible connection such as a tube, and where at least one pneumatic valve is provided between the compressed-air source and the orifice of the passage and adapted when operated by the examining/treating dentist to be opened and closed selectively to admit or shut off air through the passage, and, if necessary, selectively to vary the volume of air passed therethrough.

This will save the dentist from simultaneously or consecutively having to concentrate on the examination by means of the explorer and on directing the nozzle of the chip blower towards the tooth section examined, and he is therefore able to give his full attention to the examination by means of the explorer. It has been found that the light flexible connection between explorer and compressed-air source does not interfere with the actual examination work by means of the explorer.

In a preferred embodiment of the dental explorer according to the invention the explorer portion is removably attached to the handle or butt. This has the advantage that only the removable explorer portion requires cleaning and sterilization every time it is used, i.e. after each patient examined by means of the explorer. The removable attachment can be designed in any known suitable manner that will ensure a rigid connection between the explorer portion and the handle or butt.

Preferably, there are provided a plurality of identical or different explorer portions adapted to be removably and interchangeably attached to one and the same handle or butt. In the first place, this ensures that a number of explorer portions can be sterilized simultaneously and that such sterilization need not be made for every new patient examined, and secondly, that the same handle or butt can be fitted with explorer portions of different configuration and properties as required.

In a preferred embodiment of the dental explorer according to the invention that part of the passage belonging to the explorer portion is provided therein in its entirety. This is a simple, sturdy and inexpensive design as it makes it possible to manufacture the explorer portion from commercially available tube material.

In a second embodiment of the dental explorer according to the invention the passage or at least that part proximate its orifice is separate from the explorer portion. This makes it possible to impart the explorer point a higher degree of resiliency relatively to the handle or butt. Preferably, that part of the passage proximate its orifice is adjustable in relation to the explorer point. This makes it possible to direct the air jet selectively in relation to the tooth area examined. Preferably, at least the explorer portion is made from thermic sterilizable material to ensure that the explorer portions can be sterilized together with the instruments and parts thereof otherwise used for dental treatment.

In a preferred embodiment of the dental explorer according to the invention the explorer portion is bent or wound in conventional manner so that its point forms an angle to the longitudinal axis of the handle or butt. This ensures that, as stated by way of introduction, the explorer point can be used on tooth surfaces hard to get at.

In another preferred embodiment of the dental explorer according to the invention the pneumatic or one pneumatic valve is arranged in the handle or butt and adapted to be operated by the touch of a finger. Preferably, the valve consists of a valve seat arranged in axial symmetry in the handle or butt, said valve seat having an axial bore and generally concave seat surface, and a valve body in axial position when the valve is closed and having a convex valve surface whose convexity is greater than the concavity of the seat surface of the valve seat, means for resiliently urging the valve surface against the seat surface, and means adapted by manual operation to cause displacement of the valve body away from its axial closed position. The arrangement of the pneumatic valve or one of the pneumatic valves in the handle will achieve a particularly simple construction of the dental explorer according to the invention as this will eliminate any external valves such as foot valves or pedal switch magnetic valves. The particular configuration of the seat surface of the valve seat and the valve surface of the valve body makes possible selective adjustment of the flow area of the valve and at the same time that the valve body is returned to its closed position when manual operation of the valve is discontinued.

Preferably, the concave seat surface of the valve seat is a truncated cone face having an apex angle preferably greater than 120°, and the valve body is a ball with a diameter less than that of the seat surface of the valve seat but several times greater than the diameter of the bore therein, or the valve surface of the valve body is a ball segment face forming part of such a ball, and where there are provided means adapted by manual actuation of a grip arranged on the outside of the handle or butt by engagement against the valve body to displace same away from its axial closed position. In practice this configuration of the valve has proved satisfactory from an operational point of view and is simple and inexpensive to manufacture from an technical point of view.

The invention will be further described below based on embodiments, reference being made to the drawings, in which FIG. 1 is an enlarged broken longitudinal view of a dental explorer according to the invention, FIG. 2 another embodiment of an explorer portion for attachment to the handle or butt shown in FIG. 1, FIG. 3 an enlarged cut generally between the lines III—III in FIG. 1 of the valve structure used, and FIG. 4 a cut taken along the line IV—IV of FIG. 3.

The dental explorer shown in FIG. 1 comprises a handle or butt generally designated 1 and an explorer portion generally designated 2. In the embodiment shown the explorer portion 2 is attached to the handle 1 by means of a knurled union nut 3 screwed onto an intermediate piece 4 having an external thread and which by means of a shoulder 5 engaging a flange 6 on the explorer portion 2 maintains the latter in engagement against the intermediate piece 4. A passage generally designated 7 extends through part of the explorer portion 2, through the intermediate piece 4 and the handle 1. The explorer portion 2 has two bends so as to show a winding or an elbow, its point 8 forming an angle of about 45° to the longitudinal axis of the handle. The passage 7 terminates in the explorer portion 2 spaced from and oriented towards the point 8 at 9, and that part of the explorer located between the orifice 9 and the point 8 is generally tapered, i.e. it shows a diminishing cross section in the said direction. A packing lo is provided around the passage 7 between the explorer portion 2 and the intermediate piece 4. The end of the handle 1 furthest away from the explorer portion 2 is provided with a tube branch 11 connected by means of a suspended, not shown, light and flexible tube to a likewise not shown compressed-air source. This source may be that which is conventional in dental clinics or may be a separate air compressor having a relatively small output at a relatively low pressure, or may consist of a compressed-air bottle in connection with a suitable pressure-reducing valve. At the opposite end of the handle 1 the passage 7 is extended by a bore 12 of greater diameter. The outer end of the bore 12 is provided with an internal thread for accommodating the intermediate piece 4 which has a projecting portion provided with a similar, external thread. The bore 12 has a coil spring 13 one end of which engages the bottom of the bore 12 within a recess 14 therein. The opposite end of the coil spring 13 engages a ball 15, urging same against a valve seat 16 which in the embodiment shown is arranged in a recess in the intermediate piece 4. The more specific configuration of the valve structure appears with greater clarity from FIG. 3, from which will be noted that the valve seat 16 arranged in axial symmetry in the intermediate piece 4 has a narrow, continuous and axial bore 17 and a concave seat surface facing the ball and shown in the figure as a cone surface having a wide apex angle. Throughout the length of the wall of the bore 12 there is provided a recess 18 longitudinally of the bore 12 and in which is arranged a rod-like valve opener 19 of generally rectangular cross section. In the recess 14 the valve opener 19 engages a turn of the coil spring 13 to form a pivot centre about which the rod-like valve opener 19 can perform a pivoting movement in the bore 12. The valve opener 19 further includes a projecting portion 20 which displaceably therein is passed through an opening in the handle or butt 1 from the bore 12 therein to its outside to project therefrom. By a fastening means such as a rivet 22 a grip 21 in the form of a leaf spring it attached to the outside of the handle or butt 1 and lightly engages the projection 20 of the valve opener 19.

The mode of operation of the valve shown is as follows:

By lightly depressing the grip 21 with a finger the projection 20 on the valve opener 19 is urged inwardly against the bore 12 in the handle 1. This will cause the valve opener 19 to pivot about its right end in FIG. 1, and its opposite end will engage the ball 15 to force it away from its closed position on the valve seat 16 as shown in FIGS. 1 and 3 against the action of a power component deriving from the coil spring 13. This will allow air from the compressed-air source to pass through the bore 17 in the valve seat 16 and further through the passage 7 in the intermediate piece 4 and the explorer portion 2. A light touch of the grip 21 and small movements thereof will thus admit more or less air through the bore 17. When the grip 21 is released, the action of the coil spring 13 will return the ball 15 along the concave seat surface of the valve seat 16 to its closed position as the valve opener 19 simultaneously swings back to its initial position.

FIG. 2 shows another embodiment of the explorer portion 2' which is specially designed for use when it is important for the examination by means of the dental explorer that its point 8' be resilient relatively to the handle or butt 1. The explorer portion 2' is interchangeable with the explorer portion 2 and like the latter attachable to the handle or butt 1 by means of a knurled union nut 3. The explorer portion 2' distinguishes from the explorer portion 2 in that the part 7' of the passage 7 proximate the orifice 9' is in the form of a tubular nozzle portion 23 which is separate from the explorer portion 2. This makes it possible to impart to the tapered part of the explorer portion, which terminates in the point 8', a more elongate and slender form to increase its resiliency. The nozzle portion 23 may be pivotable relatively to the explorer portion 2' so as to make the orientation of its orifice 9' adjustable in relation to the explorer point 8'.

The invention is not restricted to the embodiments shown in the drawings and described above but also includes such modifications as will be obvious to one skilled in the art within the scope of the directions of the accompanying claims.

What is claim is:

1. In a dental explorer assembly for use in dentistry, the explorer including a handle or butt portion and a generally tapered explorer portion terminating in a point which is to be brought into contact with surfaces of teeth of a patient, the improvement comprising a passage having a first orifice and a second orifice, said passage extending at least partially through said handle or butt portion with said first orifice spaced from and directed toward said point for directing a stream of compressed air onto surface of a tooth adjacent said point to blow away chips and maintain this surface dry; a compressed-air source; a light and flexible connection connected between said second orifice of said passage and said compressed air source for feeding compressed air to said passage; at least one valve arranged in said handle or butt portion between said compressed-air source and said first orifice for selectively allowing compressed air to flow through said passage under control of one using the assembly, said valve including a valve seat arranged in axial symmetry in said handle or butt portion and having (1) an axial bore and generally concave seat surface and (2) a valve body in axial position when said valve is closed and having a convex valve surface whose convexity is greater than concavity of said seat surface of said valve seat; means for resiliently urging said valve surface against said seat surface; and finger-operable means for causing displacement of said valve body away from its axial closed position.

2. An improved dental explorer assembly according to claim 1, wherein said at least one valve comprises a valve for selectively varying the volume of air passing through said passage.

3. An improved dental explorer assembly according to claim 1, wherein said explorer portion is removably attached to said handle or butt portion.

4. An improved dental explorer assembly according to claim 3, including a plurality of removable and interchangeable explorer portions for selective attachment to said handle or butt portion.

5. An improved dental explorer assembly according to claim 1, wherein a portion of said passage is provided within said explorer portion.

6. An improved dental explorer assembly according to claim 1, wherein a portion of said passage proximate said first orifice is separate from said explorer portion.

7. An improved dental explorer assembly according to claim 6, wherein said portion of said passage proximate said first orifice is adjustable in relation to said point of said explorer portion.

8. An improved dental explorer assembly according to claim 1, wherein at least said explorer portion is made from thermic sterilizable material.

9. An improved dental explorer assembly according to claim 1, wherein said explorer portion is configured in conventional manner, said point forming an angle with respect to the longitudinal axis of said handle or butt portion.

10. An improved dental explorer assembly according to claim 1, wherein said concave seat surface of said valve seat is a truncated cone face having an apex angle, wherein said valve body is a ball having a diameter less than that of said seat surface of said valve seat and several times greater than the diameter of said bore therein.

11. An improved dental explorer assembly according to claim 1, wherein said apex angle is greater than 120°.

12. An improved dental explorer assembly according to claim 1, wherein said valve body is a ball and said valve surface of said valve body is a ball segment face forming part of said ball.

* * * * *